(12) United States Patent
Salz et al.

(10) Patent No.: US 9,339,443 B2
(45) Date of Patent: May 17, 2016

(54) DENTAL RESTORATIVE MATERIAL BASED ON AN ANTIMICROBIALLY ACTIVE COMPOUND

(75) Inventors: Ulrich Salz, Lindau (DE); Thorsten Bock, Feldkirch (AT); Christoph Peter Fik, Lahr/Schwarzwald (DE); Jörg Tiller, Herdecke (DE); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 961 days.

(21) Appl. No.: 13/368,998

(22) Filed: Feb. 8, 2012

(65) Prior Publication Data

US 2012/0208917 A1  Aug. 16, 2012

(30) Foreign Application Priority Data

Feb. 15, 2011 (EP) ..................................... 11154589

(51) Int. Cl.
*A61K 6/083* (2006.01)
*A61K 6/00* (2006.01)
*A61K 6/093* (2006.01)

(52) U.S. Cl.
CPC ............. *A61K 6/0023* (2013.01); *A61K 6/0008* (2013.01); *A61K 6/0017* (2013.01); *A61K 6/0067* (2013.01); *A61K 6/083* (2013.01); *A61K 6/093* (2013.01)

(58) Field of Classification Search
CPC .............................. A61K 6/0067; A61K 6/083
See application file for complete search history.

(56) References Cited

U.S. PATENT DOCUMENTS

| | | | |
|---|---|---|---|
| 5,358,688 A | 10/1994 | Robertson | |
| 5,408,022 A | 4/1995 | Imazato et al. | |
| 5,494,987 A | 2/1996 | Imazato et al. | |
| 5,520,910 A | 5/1996 | Hashimoto et al. | |
| 5,536,861 A | 7/1996 | Robertson | |
| 5,733,949 A | 3/1998 | Imazato et al. | |
| 6,162,056 A | 12/2000 | Mannschedel | |
| 6,316,015 B1* | 11/2001 | Rondelez et al. | 424/409 |
| 7,553,881 B2* | 6/2009 | Salz et al. | 523/116 |
| 2002/0012634 A1 | 1/2002 | Pflug et al. | |
| 2003/0064102 A1 | 4/2003 | Nakatsuka | |
| 2003/0220416 A1 | 11/2003 | Montgomery et al. | |
| 2005/0261169 A1 | 11/2005 | Enderle et al. | |
| 2007/0254979 A1 | 11/2007 | Salz et al. | |
| 2007/0273331 A1 | 11/2007 | Cross et al. | |
| 2008/0207581 A1* | 8/2008 | Whiteford et al. | 514/183 |
| 2008/0226585 A1 | 9/2008 | Bouloussa et al. | |
| 2010/0041786 A1* | 2/2010 | Qian | 522/154 |
| 2010/0098738 A1 | 4/2010 | Milner et al. | |
| 2010/0254149 A1 | 10/2010 | Gill | |
| 2011/0064977 A1 | 3/2011 | Wendel et al. | |
| 2011/0123475 A1 | 5/2011 | Dias et al. | |
| 2011/0275675 A1* | 11/2011 | Rist et al. | 514/332 |

FOREIGN PATENT DOCUMENTS

| | | |
|---|---|---|
| CA | 2304166 A1 | 4/1999 |
| CA | 2383181 A1 | 11/2002 |
| DE | 102008036520 A1 | 2/2010 |
| JP | 2002200100 A | 7/2002 |
| JP | 2002236312 A | 8/2002 |
| JP | 3100119 U | 4/2004 |
| JP | 2004230122 A | 8/2004 |
| JP | 2008061469 A | 3/2008 |
| JP | 2010011668 A | 1/2010 |
| WO | 2006101438 A1 | 9/2006 |

OTHER PUBLICATIONS

Waschinski, Christian J., et al., "Influence of Satellite Groups on Telechelic Antimicrobial Functions of Polyoxazolines," Macromolecular Bioscience, 2005, 5, 149-156, Freiburg Materials Research Center and Institute for Macromolecular Chemistry, University of Freiburg, Germany.

* cited by examiner

*Primary Examiner* — Michael Pepitone
(74) *Attorney, Agent, or Firm* — Ann M. Knab; Thad McMurray

(57) ABSTRACT

The invention relates to a dental restorative material which comprises (a) at least one antimicrobially active compound of Formula (I)

$$[AG]_m\text{-}R^1\text{—}Z\text{—}SP\text{—}Y\text{—}R^2\text{—}[WG]_p \qquad (I),$$

or a filler that is surface-modified with at least one compound of Formula (I), (b) at least one radically polymerizable monomer and (c) at least one initiator for the radical polymerization. The invention also relates to a use of such dental restorative material for the preparation of an adhesive, primer, cement, coating material or filling material.

The invention also relates to a dental material which comprises at least one compound of Formula (I), as well as a use of a compound of Formula (I) for modifying the surface of a substrate selected from ceramic materials, noble and non-noble metals, hard tooth structure, tooth enamel, dentine, collagen, soft tissue, mucous membrane and leather.

24 Claims, No Drawings

DENTAL RESTORATIVE MATERIAL BASED ON AN ANTIMICROBIALLY ACTIVE COMPOUND

CROSS-REFERENCE TO RELATED APPLICATIONS

This application claims the benefit of European Patent Application No. 11154589.3 filed Feb. 15, 2011, which is hereby incorporated by reference in its entirety.

TECHNICAL FIELD

The present invention relates to dental materials and dental restorative materials based on a compound with antimicrobial effect.

BACKGROUND

Giving dental restorative materials antimicrobial properties has long been known and is usually carried out by the purely physical mixing of an antimicrobial active ingredient into a corresponding material matrix. Thus for example in WO 98/48766 and correspondding US published application US2002012634, which is hereby incorporated by reference, tooth-coating material for the prevention of caries is described which contains triclosan (2,4,4'-trichloro-2'-hydroxydiphenylether) as antimicrobial active ingredient. Materials for dental use such as prosthetic plastics and fixing cements which contain antimicrobial phenolic substances such as triclosan are also described in US 2003/0220416, which is hereby incorporated by reference.

DE 19813686 and corresponding U.S. Pat. No. 6,162,056, which is hereby incorporated by reference, disclose a gutta-percha-based root-canal filling material which releases chlorhexidine as antimicrobial active ingredient.

Several problems are associated with the purely physical mixing of antimicrobial active ingredients into a material. In order to achieve its antimicrobial effect, the active ingredient must be released over the period of action of the material. As a rule, the release rates are such that the active ingredient is initially released in a very high concentration and thereafter the antimicrobial effect is largely lost. Another disadvantage is that toxic side-effects can occur at high active ingredient concentrations, which is undesirable in particular in medical applications. For this reason, there has been a switch, for such applications in particular, to making the active ingredient polymerizable in order to immobilize it during the curing of the material by homopolymerization or copolymerization with another polymerizable monomer in the forming polymer.

U.S. Pat. No. 5,536,861 and U.S. Pat. No. 5,358,688, which are hereby incorporated by reference, disclose organosilicone monomers which contain a quaternary ammonium group as antimicrobial group for use in contact lenses.

EP 0663409 and corresponding U.S. Pat. No. 5,520,910, which is hereby incorporated by reference, discloses monomers which contain quaternary phosphonium groups as active group for use in contact lenses.

In EP 0537774, and corresponding U.S. Pat. No. 5,408,022 and U.S. Pat. No. 5,494,987, which are hereby incorporated by reference, polymerizable active-ingredient monomers which contain a quaternary ammonium group are described. (Meth)acryl functionalities are used as polymerizable group, an alkylene spacer with 2 to 18 C atoms being located between the polymerizable group and the active group.

In EP 0705590 and corresponding U.S. Pat. No. 5,733,949, which is hereby incorporated by reference, and WO 01/90251, special compositions for dental use which contain an antimicrobial, polymerizable monomer according to EP0537774 and corresponding U.S. Pat. No. 5,408,022 and U.S. Pat. No. 5,494,987, are described.

A disadvantage when using polymerizable active ingredient monomers is that in most cases only the monomer has an antimicrobial effect, which is lost after the polymerization. Often, only residual monomer present is responsible for the antimicrobial effect of the polymers, with the result that after the elution of the non-polymerized antimicrobial monomers the antimicrobial effect of the materials diminishes. The antimicrobial long-term effect is thus significantly reduced, as a result of which e.g. drugs or medicinal products lose at least some of their clinical capability.

EP 1849450 and corresponding US Published Application 2007254979, which is hereby incorporated by reference, discloses dental materials equipped with an antimicrobially active macromer wherein an antimicrobially active group is bonded to a radically polymerizable group via a polymeric spacer and which displays a high anti-microbial efficacy also after polymerization.

U.S. Pat. No. 6,316,015, which is hereby incorporated by reference, describes substrates to the surfaces of which molecules with antibiotic, bactericidal, virucidal or fungicidal properties are covalently bonded, such as e.g. catheters, syringes, needles and tubes for medical applications.

EP 1707601 and corresponding US Published Application 2008226585, which is hereby incorporated by reference, describes a method of treating surfaces, wherein a statistical copolymer is bonded to the surface in order to give the latter cytotoxic or cell-adhesion properties. The statistical copolymer has at least one monomer unit A, the reactive site of which can form covalent bonds with the substrate, and a monomer unit B, which comprises at least one antimicrobial, antiviral or fungicidal molecule. The method is said to be useful for the antiseptic treatment of various substrates, such as for example plastics, wood, paper or textiles and in particular in the field of personal hygiene, in the clinical field as well as for domestic use and in the food industry.

SUMMARY

It is an object of the invention to provide dental materials and dental restorative materials which have a long-lasting, high antimicrobial effect and which do not have the named disadvantages.

This object is achieved according to the invention by dental materials and dental restorative materials which comprise at least one antimicrobially active compound of Formula (I) as defined below.

DETAILED DESCRIPTION

In a first aspect, the invention relates to an antimicrobially active compound of Formula (I):

wherein the variables have the following meanings:
m=1, 2, 3 or 4;
p=1, 2 or 3;
$R^1$=is absent or a linear or branched $C_1$ to $C_{20}$ alkylene radical which can be interrupted one or more times by O, S, NH, $N^+R^3{}_2$, $SiR^3{}_2$, $OSiR^3{}_2$, CONH, $CONR^3$, COO and/or OCONH, a substituted or unsubstituted, aromatic $C_6$ to $C_{14}$ radical or a combination thereof;

$R^2$=is absent or a linear or branched $C_1$ to $C_{20}$ alkylene radical which can be interrupted one or more times by O, S, NH, $N^+R^3_2$, $SiR^3_2$, $OSiR^3_2$, CONH, $CONR^3$, COO and/or OCONH, a substituted or unsubstituted, aromatic $C_6$ to $C_{14}$ radical or a combination thereof;

$R^3$=in each case independently a linear or branched $C_1$ to $C_{20}$ alkyl radical, a substituted or unsubstituted phenyl or benzyl radical;

AG=an anchor group selected from:

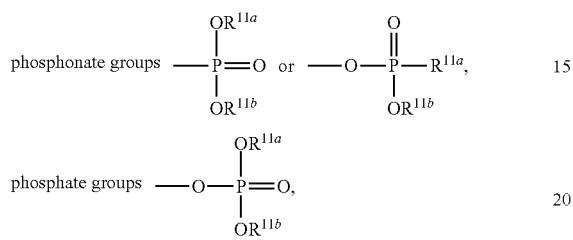

wherein $R^{11a}$ and $R^{11b}$ are independently selected from H, alkyl, aryl or —Si(alkyl)$_3$, wherein alkyl preferably represents methyl, ethyl, n-propyl or i-propyl, and wherein particularly preferably $R^{11a}$ and $R^{11b}$ are each alkyl or $R^{11a}$ is H and $R^{11b}$ is alkyl,

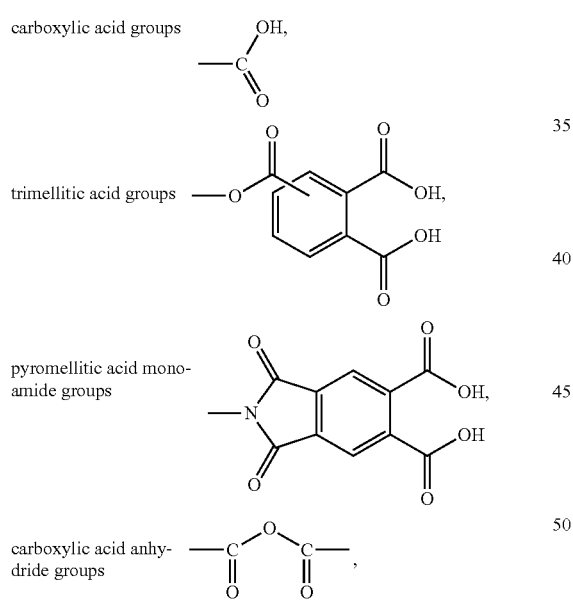

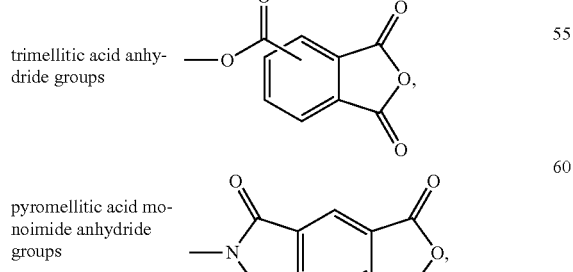

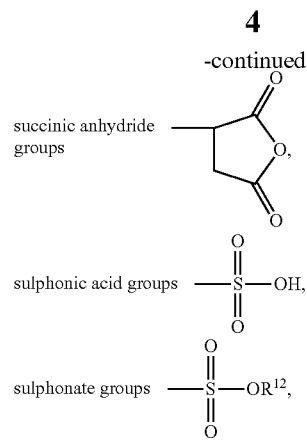

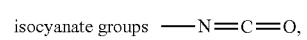

wherein $R^{12}$ represents —Si(alkyl)$_3$ and alkyl preferably represents methyl, ethyl, n-propyl or i-propyl,

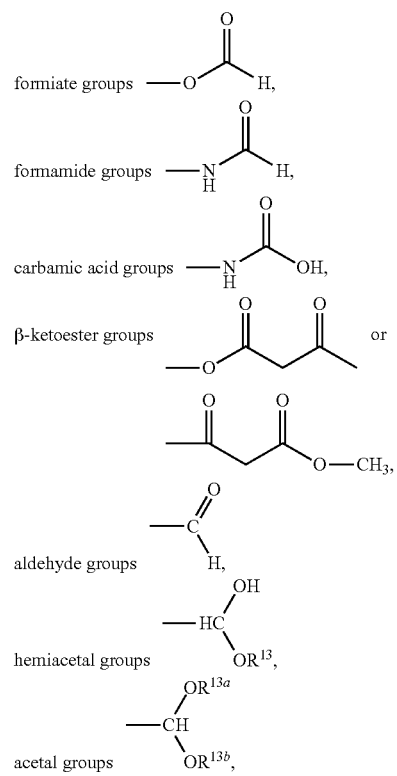

wherein $R^{13}$, $R^{13a}$ and $R^{13b}$ are independently selected from alkyl, in particular methyl, ethyl, n-propyl or i-propyl, preferably ethyl, or particularly preferably $R^{13a}$ and $R^{13b}$ connected to form a 4- to 7-membered ring system, preferably a 5-membered ring system, wherein one of the oxygen atoms can be replaced by N,

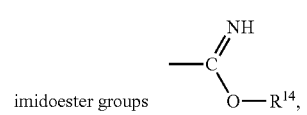

wherein $R^{14}$ is alkyl, preferably methyl, ethyl, n-propyl, i-propyl, n-butyl or t-butyl, N-hydroxysuccinimide ester groups 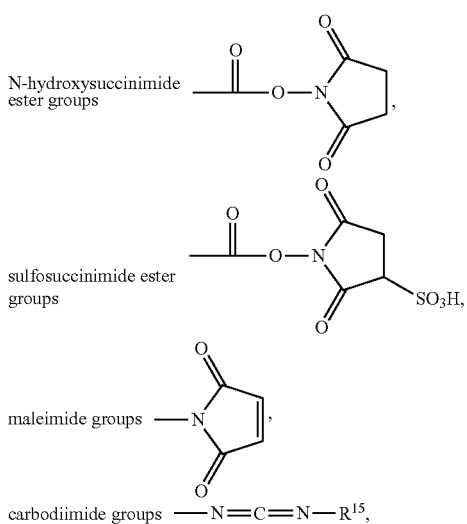

sulfosuccinimide ester groups maleimide groups carbodiimide groups —N=C=N—R$^{15}$, wherein R$^{15}$ represents an optionally substituted alkyl or cycloalkyl group and preferably represents 3-dimethylaminopropyl, i-propyl or cyclohexyl, silane groups 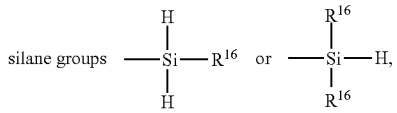

wherein R$^{16}$ is independently selected from alkoxy, aryloxy, Cl, alkyl or aryl, in particular alkoxy or aryloxy, preferably methoxy, ethoxy or propoxy and particularly preferably methoxy, silyl groups 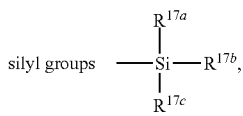

wherein R$^{17a}$ is selected from alkoxy, aryloxy, Cl or OH, in particular alkoxy, aryloxy, preferably methoxy, ethoxy or propoxy and particularly preferably methoxy, and R$^{17b}$ and R$^{17c}$ are each independently selected from alkoxy, aryloxy, Cl, OH, alkyl or aryl, preferably alkoxy, aryloxy, alkyl or aryl, in particular alkoxy or aryloxy, preferably methoxy, ethoxy or propoxy and particularly preferably methoxy, sulphide groups —S—H disulphide groups —S—S—R$^{18}$ wherein R$^{18}$ is selected from alkyl, aryl or arylalkyl, preferably methyl, ethyl, n-propyl, i-propyl, n-butyl, t-butyl, phenyl, biphenyl or alkylphenyl, thiophosphonate groups 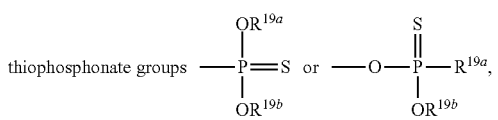

thiophosphate groups 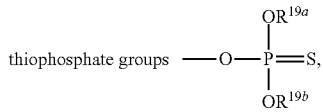

wherein R$^{19a}$ and R$^{19b}$ are selected independently from H, alkyl, aryl or —Si(alkyl)$_3$, wherein alkyl preferably represents methyl, ethyl, n-propyl or i-propyl, and wherein particularly preferably R$^{19a}$ and R$^{19b}$ are each alkyl or R$^{19a}$ is H and R$^{19b}$ is alkyl, thiocarboxylic acid groups, in particular 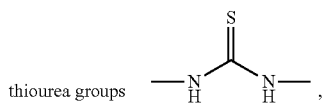

wherein R$^{20}$ represents an optionally substituted alkyl group and preferably represents —CH$_2$—CH$_2$—NH$_2$ or —CH$_2$—CH(NH$_2$)—COOH, thiourea groups 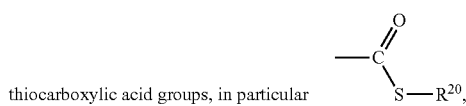

triazine thione groups, in particular 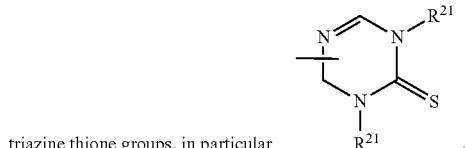

triazine dithione groups, in particular 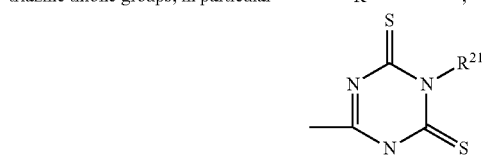

thiouracil groups, in particular 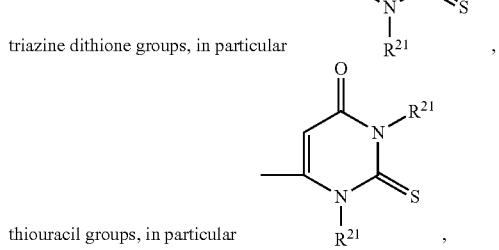

wherein R$^{21}$ is in each case independently selected from H or alkyl, preferably methyl, ethyl, n-propyl or i-propyl;

SP=a polymeric spacer which is preferably selected from polyethylene glycol groups, polypropylene glycol groups, polyglycerol groups, polyalkyloxazoline groups, polyethyleneimine groups, polyacrylic acid groups, polymethacrylic acid groups, polyvinyl alcohol groups, polyvinyl acetate groups, poly-(2-hydroxyethyl)acrylate groups, poly-(2-hydroxyethyl)methacrylate groups, hydrophilic polypeptide groups, polyoxazoline groups, polyalkylene groups, polyester groups, polyamide groups, polyurea groups, polyurethane groups, polycyanoacrylate groups, polyacrylate groups, polyacrylic ester groups, polymethacrylate groups, polymethacrylic ester groups, N-alkylated polyethyleneimine groups, N-alkylated vinylpyridine groups, polysaccharide groups, polyaminosaccharide groups, and copolymers of the corresponding monomers;

WG=an antimicrobially active group;

Y=is absent, O, S, NH, $N^+R^3{}_2$, an ester, amide or urethane group,

Z=is absent, O, S, NH, $N^+R^3{}_2$ an ester, amide or urethane group.

The compounds of Formula (I) according to the above definition generally comprise a polymeric spacer SP, which is preferably in each case terminally bonded to one or more anchor groups AG and one or more active ingredient groups WG.

The substituents optionally present in $R^1$, $R^2$ and $R^3$ are preferably selected independently of one another from ($C_1$-$C_6$)alkyl, ($C_1$-$C_6$)alkoxy, aryl, benzyl, F, Cl, Br, I, OH, —COOH, —COO—($C_1$-$C_6$)alkyl, —CONH$_2$, —COR$^4$ and —COOR$^4$, wherein $R^4$ is a ($C_1$-$C_{20}$)alkyl, phenyl or benzyl radical.

Formula (I) covers only compounds which are compatible with the theory of chemical valence. The indication that a radical can be interrupted for example by O, S, NH, $SiR^3{}_2$, CONH, $CONR^3$, COO, OCONH etc. is to be understood to mean that these atoms or groups are inserted into the carbon chain of the radical, i.e. are bordered on both sides by carbon atoms. The number of these foreign atoms or groups is therefore at least 1 less than the number of carbon atoms, and the foreign atoms or groups cannot be in terminal position.

By combinations of alkylene radicals and aromatic groups are preferably meant alkylene-arylene, alkylene-arylene-alkylene and arylene-alkylene-arylene groups, in particular —CH$_2$-Ph- and —CH$_2$-Ph-CH$_2$— groups.

If there are several anchor groups AG in the compound of Formula (I) (m=2, 3 or 4), the anchor groups form multifunctional anchor groups together with atoms of the radical $R^1$. The anchor groups AG can be the same or different. In a preferred embodiment, the anchor groups are the same.

Examples of multifunctional anchor groups are di-, tri- and tetracarboxylic acid groups, preferably tricarboxylic acid groups, bisphosphonate and bisphosphate groups, bis(imido ester) groups, in particular

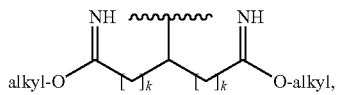

wherein k is independently 1 to 4, preferably dialkyl adipimidate groups, and bis(sulfosuccinimidyl ester) groups, in particular

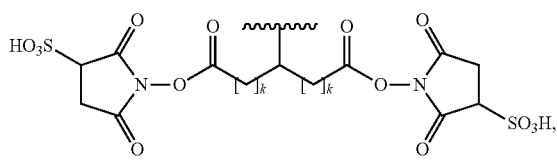

wherein k is independently 1 to 4, preferably bis(sulfosuccinimidyl)suberate groups.

If there are several antimicrobially active groups WG in the compound of Formula (I) (p=2 or 3), these can also be the same or different. In a preferred embodiment of the compound of Formula (I), the antimicrobially active groups WG are the same.

In a further preferred embodiment, m=1 and p=1 and the anchor group AG and active ingredient group WG are each in terminal position.

The term polymeric spacer here generally comprises spacers with at least 3, in particular 3 to 500, preferably 5 to 200, particularly preferably 10 to 100, most preferably 10 to 50 repeating units.

The compound of Formula (I) preferably has a molecular weight of at least 250 g/mol, in particular at least 500 g/mol, preferably at least 1000 g/mol, particularly preferably at least 1500 g/mol.

In a further preferred embodiment of the compound of Formula (I) according to the invention, $R^1$ and/or $R^2$ is a linear or branched $C_5$ to $C_{20}$ alkylene radical and particularly preferably a $C_{10}$ to $C_{20}$ alkylene radical.

In a preferred embodiment, AG is selected from phosphonate, phosphate, trimellitic acid, pyromellitic acid monoimide, carboxylic acid anhydride, trimellitic acid anhydride, pyromellitic acid monoimide anhydride, succinic anhydride, sulphonic acid, sulphonate, isocyanate, formiate, formamide, carbamic acid, β-ketoester, imidoester, N-hydroxysuccinimide ester, sulfosuccinimide ester, maleimide, carbodiimide, sulphide, disulphide, thiophosphonate, thiophosphate, thiocarboxylic acid, thiourea, triazine thione, triazine dithione and thiouracil groups.

In addition, embodiments wherein AG is selected from phosphonate, in particular dialkylphosphonate, phosphate, carboxylic acid, carboxylic acid anhydride, sulphonic acid, alkoxysilane and aldehyde groups are particularly preferred. Multifunctional carboxylic acid groups, in particular di-, tri- and tetracarboxylic acid groups, carboxylic acid anhydride groups and phosphonate groups are most preferred.

In a further preferred embodiment AG is selected from phosphonate, phosphate, carboxylic acid, trimellitic acid, pyromellitic acid monoimide, carboxylic acid anhydride, trimellitic acid anhydride, pyromellitic acid monoimide anhydride, succinic anhydride, sulphonic acid and sulphonate groups, preferably phosphonate groups, in particular dialkylphosphonate, phosphate, carboxylic acid, carboxylic acid anhydride and sulphonic acid groups, most preferably multifunctional carboxylic acid groups, in particular di-, tri- and tetracarboxylic acid groups, carboxylic acid anhydride groups and phosphonate groups. Such anchor groups are particularly suitable for the modification of tooth enamel, dentine as well as substrates based on metal oxides.

In another embodiment, AG is selected from isocyanate, formiate, formamide, carbamic acid, β-ketoester, aldehyde, hemiacetal, acetal, imidoester, N-hydroxysuccinimide ester, sulfosuccinimide ester, maleimide and carbodiimide groups. Such anchor groups are particularly suitable for the modification of collagen and other protein based substrates.

In another preferred embodiment, AG is selected from silane groups —SiHR$^{16}{}_2$ or —SiH$_2$R$^{16}$. Such anchor groups are particularly suitable for modifying ethenylically unsaturated surfaces.

In another preferred embodiment, AG is selected from silyl groups —SiR$^{17a}$R$^{17b}$R$^{17c}$. Such anchor groups are particularly suitable for the modification of inorganic fillers and substrates based on oxides, for example ceramic materials. If $R^{17a}$, $R^{17b}$ and/or $R^{17c}$ are OH, the above definition can optionally also include condensation products of the corresponding silanols. These are preferably condensation products which are soluble in a polymerizable dental restorative material according to the second aspect of the invention.

In a further preferred embodiment, AG is selected from sulphide, disulphide, thiophosphonate, thiophosphate, thiocarboxylic acid, thiourea, triazine thione, triazine dithione and thiouracil groups. Such anchor groups are particularly suitable for modifying the surfaces of metallic substrates, in particular noble metals of groups 10 to 12 of the periodic table such as gold.

The antimicrobial group (WG) is preferably a primary, secondary, or tertiary amino group, a cationic primary, secondary, tertiary or quaternary ammonium group, phosphonium group or sulphonium group, a bisguanidine group, an antimicrobial peptide and/or a phenol or polyphenol radical.

By cationic primary, secondary, tertiary and quaternary ammonium groups are meant groups of the formula (—N$^+$H$_3$), (—N$^+$H$_2$R), (—N$^+$HR$_2$), and (—N$^+$R$_3$) with R=n-alkyl, wherein the radicals R can in each case be the same or different and wherein also two radicals R together can form a saturated or unsaturated, arouratic or non-aromatic, mono- or polycyclic ring system which can be unsubstituted or substituted. By a cationic quaternary ammonium group is moreover meant saturated or unsaturated, aromatic or non-aromatic, mono- or polycyclic ring systems which comprise one or more quaternary nitrogen atoms, wherein the ring systems and/or the nitrogen atoms can be unsubstituted or substituted. Possible substituents are selected from H and a linear or branched C$_1$ to C$_{31}$ alkyl radical. The same applies accordingly to primary, secondary, tertiary and quaternary phosphonium groups with the formulae (—P$_3$), (—P$^+$H$_2$R), (—P$^+$HR$_2$) and (—P$^+$R$_3$) and to primary, secondary and tertiary sulphonium groups with the formulae (—S$^+$H$_2$), (—S$^+$HR) and (—S$^+$R$_2$).

In a preferred embodiment of the compound of Formula (I) according to the invention, the antimicrobially active group WG is a pyridinium group of formula

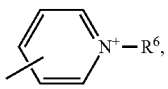

which is attached in ortho, meta or para position and particularly preferably in para position to the rest of the compound of Formula (I), or a pyridinium group of formula

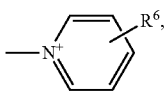

which can be substituted with R$^6$ in ortho, meta or para position and particularly preferably in para position, wherein R$^6$ in each case independently represents H or a linear or branched C$_1$ to C$_{20}$ alkyl radical.

In a further preferred embodiment,
WG=—N$^+$R$^7$R$^8$R$^9$ A$^-$, with
- R$^7$=H, a linear or branched C$_1$ to C$_{20}$ alkyl radical, preferably a C$_1$ to C$_6$ alkyl radical, particularly preferably —CH$_3$;
- R$^8$=H, a linear or branched C$_1$ to C$_{20}$ alkyl radical, preferably a C$_1$ to C$_6$ alkyl radical, particularly preferably —CH$_3$;
- or R$^7$ and R$^8$ together with the nitrogen atom to which they are bonded form an aromatic or non-aromatic ring system or an aromatic or non-aromatic ring, preferably

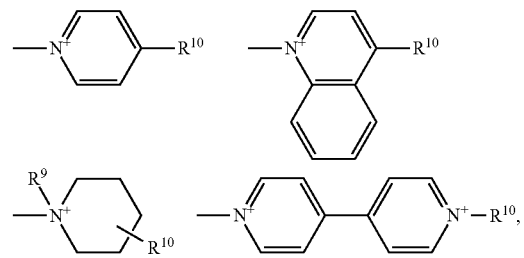

wherein R$^{10}$ is a linear or branched C$_1$ to C$_{20}$ alkyl radical;
R$^9$=is absent, H, a linear or branched C$_1$ to C$_{31}$ alkyl radical, preferably —(CH$_2$)$_r$—CH$_3$;
r=5 to 30, preferably 10 to 25, particularly preferably 10 to 20.

Furthermore, an embodiment is preferred wherein
WG=—P$^+$R$^7$'R$^8$'R$^9$' A$^-$, with
- R$^7$'=H, a linear or branched C$_1$ to C$_{20}$ alkyl radical, preferably a C$_1$ to C$_6$ alkyl radical, particularly preferably —CH$_3$;
- R$^8$'=H, a linear or branched C$_1$ to C$_{20}$ alkyl radical, preferably —CH$_3$;
- R$^9$'=is absent, H, a linear or branched C$_1$ to C$_{31}$ alkyl radical, preferably —(CH$_2$)$_r$—CH$_3$;
- r=5 to 30, preferably 10 to 25, particularly preferably 10 to 20.

Furthermore, an embodiment is preferred wherein

A$^-$ with
r=5 to 30, preferably 10 to 25, particularly preferably 10 to 20.

Further preferred are compounds of Formula (I) wherein WG is a quaternary alkylphosphonium or alkylsulphonium group, octenidine or a derivative thereof, chlorhexidine or another bisguanidine, triclosan or another chlorophenol, an inorganic group with anti-microbial properties, preferably an inorganic group which comprises one or more antimicrobially active metal ions such as e.g. Ag$^+$, Cu$^{2+}$, Sn$^{2+}$, Sn$^{4+}$, Zn$^{2+}$ or Al$^{3+}$, for example a stannic oxyfluoride group (—O—SnF$_3$), an antimicrobial peptide group such as e.g. a magainin group or a lingual antimicrobial peptide (LPA) group.

The antimicrobially active group WG can have a positive charge. This is balanced by A$^-$ anions. Preferred A anions are F$^-$, Cl$^-$, Br$^-$, I$^-$, triflate (Trf), mesylate (Mes), tosylate (Tos), palmitate, stearate, gluconate, hexafluorophosphate, phenolate, (meth)acrylphosphonate, phosphate, hydrogen phosphate or dihydrogen phosphate, in particular F$^-$, Cl$^-$, Br$^-$, I$^-$, triflate (Trf), mesylate (Mes) or tosylate (Tos).

Particularly preferred are compounds of Formula (I) wherein WG is a pyridinium group of formula

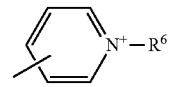

which is substituted at the quaternary nitrogen with $R^6=C_5$ to $C_{20}$ alkyl. Most preferred is a cetylpyridinium group with $R^6=C_{16}$alkyl, for example cetylpyridinium chloride or cetylpyridinium bromide.

Likewise particularly preferred are compounds of Formula (I) wherein WG is a quaternary alkylammonium group of formula

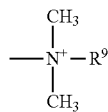

wherein $R^9$ is $C_1$ to $C_{31}$ alkyl, preferably $C_5$ to $C_{20}$ alkyl, in particular $C_7$ to $C_{18}$ alkyl, particularly preferably $C_{11}$ to $C_{16}$ alkyl and most preferably $C_{11}$ to $C_{14}$ alkyl. Most preferably, WG is an N,N-dimethyldodecylammonium group or N,N-dimethylcetylammonium group.

In a preferred embodiment, the spacer SP is selected from polyethylene glycol groups, polypropylene glycol groups, polyglycerol groups, polyalkyloxazoline groups, polyethyleneimine groups, polyacrylic acid groups, polymethacrylic acid groups, polyvinyl alcohol groups, polyvinyl acetate groups, poly-(2-hydroxyethyl)acrylate groups, poly-(2-hydroxyethyl)methacrylate groups, hydrophilic polypeptide groups,
polyoxazoline groups, polyester groups, polyamide groups, polyurea groups, polyurethane groups, polycyanoacrylate groups, polyacrylate groups, polyacrylic ester groups, polymethacrylate groups, polymethacrylic ester groups,
N-alkylated polyethyleneimine groups, N-alkylated vinylpyridine groups, polyaminosaccharide groups,
and copolymers of the corresponding monomers.

By polyaminosaccharide groups are meant here polymeric groups with aminoglycosidic repeating units. Examples of polyaminosaccharide groups are fully, partly or non-deacetylated chitosan derivatives with β-(1→4)-linked amino-2-deoxy-β-D-glucose units and similar oligosaccharides such as e.g. other aminoglycans.

In a preferred embodiment, the spacer SP is a polyoxazoline, polyester, polyamide, polyurea, polyurethane, polycyanoacrylate, polyacrylate, polyacrylic ester, polymethacrylate or polymethacrylic ester group.

In a further preferred embodiment, the spacer SP is an N-alkylated polyethyleneimine, N-alkylated vinylpyridine or polyaminosaccharide group or a cationic chitosan derivative.

Quite particularly preferably, SP is a polyoxazoline group of

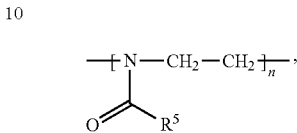

wherein n is preferably 3 to 500, preferably 5 to 200 and particularly preferably 10 to 100 and $R^5$ is preferably —$CH_3$, —$C_2H_5$ or —$C_3H_7$.

Preferred definitions of the remaining variables which can be selected independently of one another are:
m=1 or 2, particularly preferably 1;
p=1 or 2, particularly preferably 1;
$R^1$=a linear or branched $C_1$ to $C_{20}$ alkylene radical which can be interrupted one or more times by O, S, NH, $N^+R^3_2$, $SiR^3_2$, CONH, $CONR^3$, COO and/or OCONH, particularly preferably a $C_1$ to $C_{10}$ alkylene radical and most preferably —$CH_2$—$CH_2$— or —$CH_2$—$CH_2$—NH—$CH_2$—$CH_2$—;
$R^2$=a substituted or unsubstituted, aromatic $C_6$ to $C_{14}$ radical, particularly preferably phenylene or —$CH_2$-Ph-$CH_2$—;
$R^3$=a linear or branched $C_1$ to $C_{20}$ alkyl radical, in particular a $C_1$ to $C_{10}$ alkyl radical, preferably methyl, ethyl, n-propyl or i-propyl, most preferably methyl;
Y is absent, O, S, COO, particularly preferably is absent;
Z is absent, O, S, NH, $N^+R^3_2$ or amide, particularly preferably is absent, NH or $N^+(CH_3)_2$.

Compounds of Formula (I) wherein all variables have one of the preferred and in particular the particularly preferred meanings are naturally particularly preferred.

Compounds of Formula (I) that are particularly preferred according to the invention are:

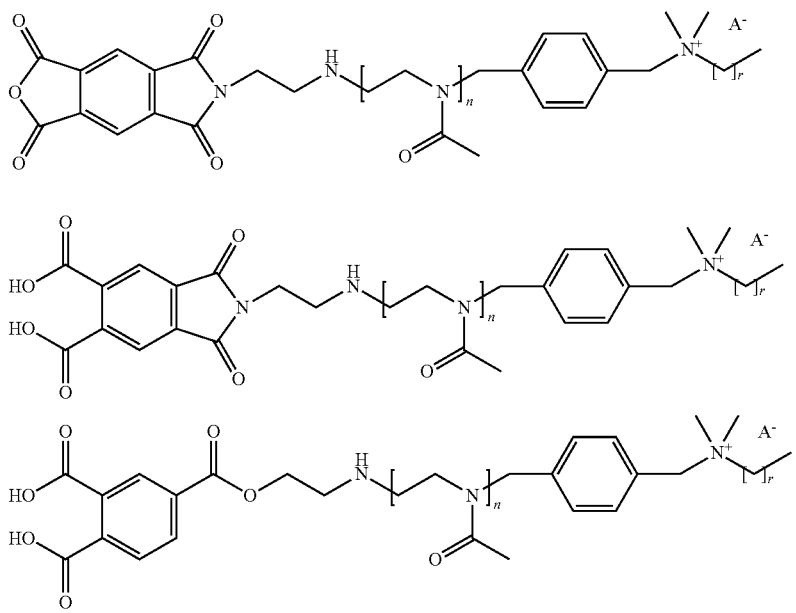

-continued
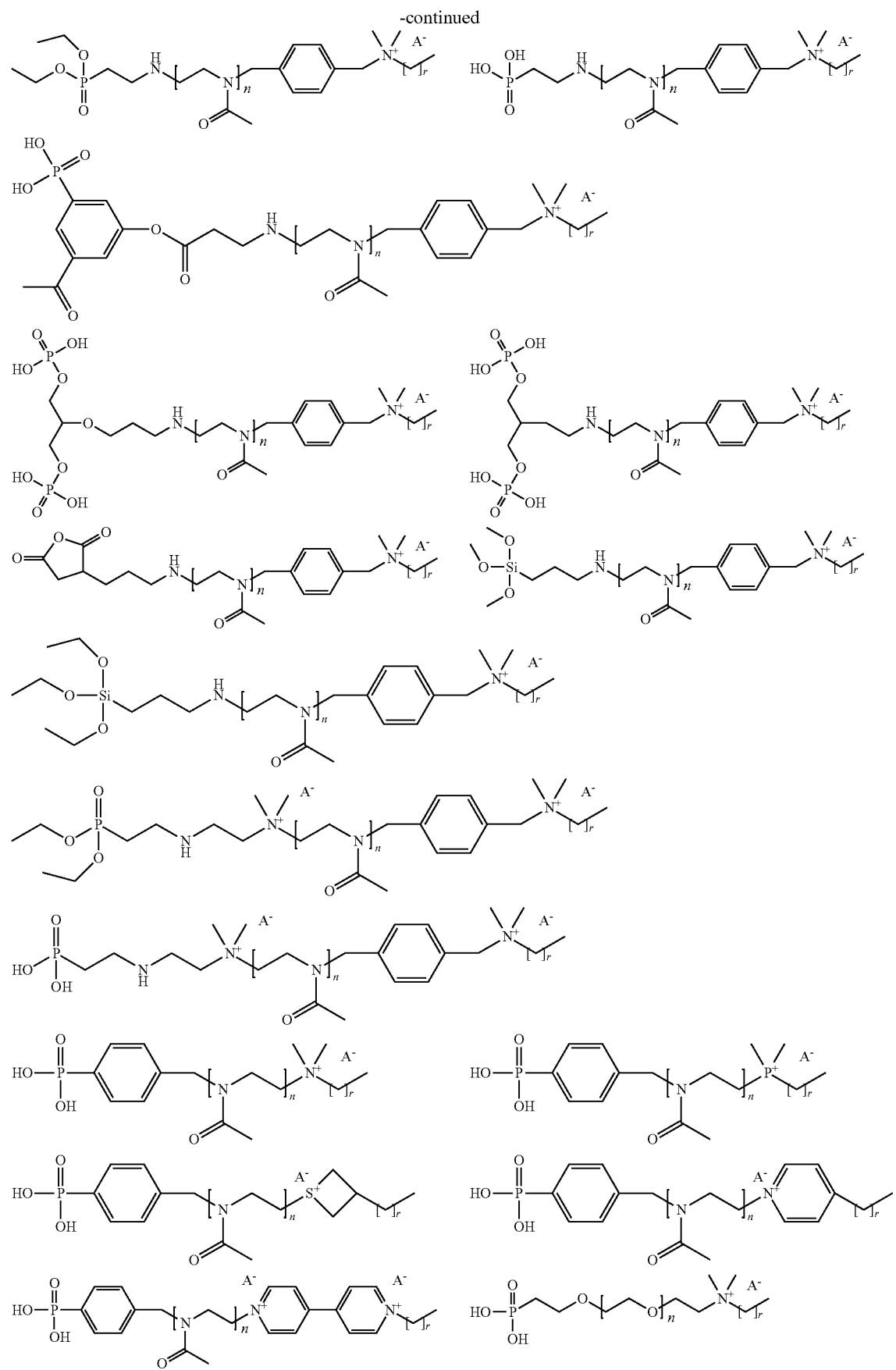

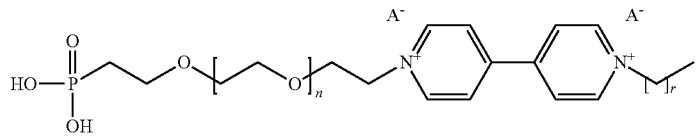

wherein
A=Cl, Br, I, Trf, Mes, Tos;
n=3 to 500;
r=10 to 20.

The compounds of Formula (I) can be prepared by multi-stage synthesis methods known per se. For example, the particularly preferred compounds of Formula (I) wherein SP is a polyoxazoline group can be prepared in the following ways. The polymeric spacer SP is built up by polymerization of 2-alkyl-1,3-oxazoline. The degree of polymerization and thus the spacer length is controlled via the monomer-initiator ratio $[M_0]/[I]$ and the reaction time.

In a first synthesis variant, a compound which comprises an anti-microbially active group WG is used as initiator. An amine that comprises an anchor group AG is preferably used to terminate the polymerization. Alternatively, for example a bifunctional amine such as ethylenediamine can be used to terminate the polymerization, the second functional group of which then serves for attachment of the anchor group AG.

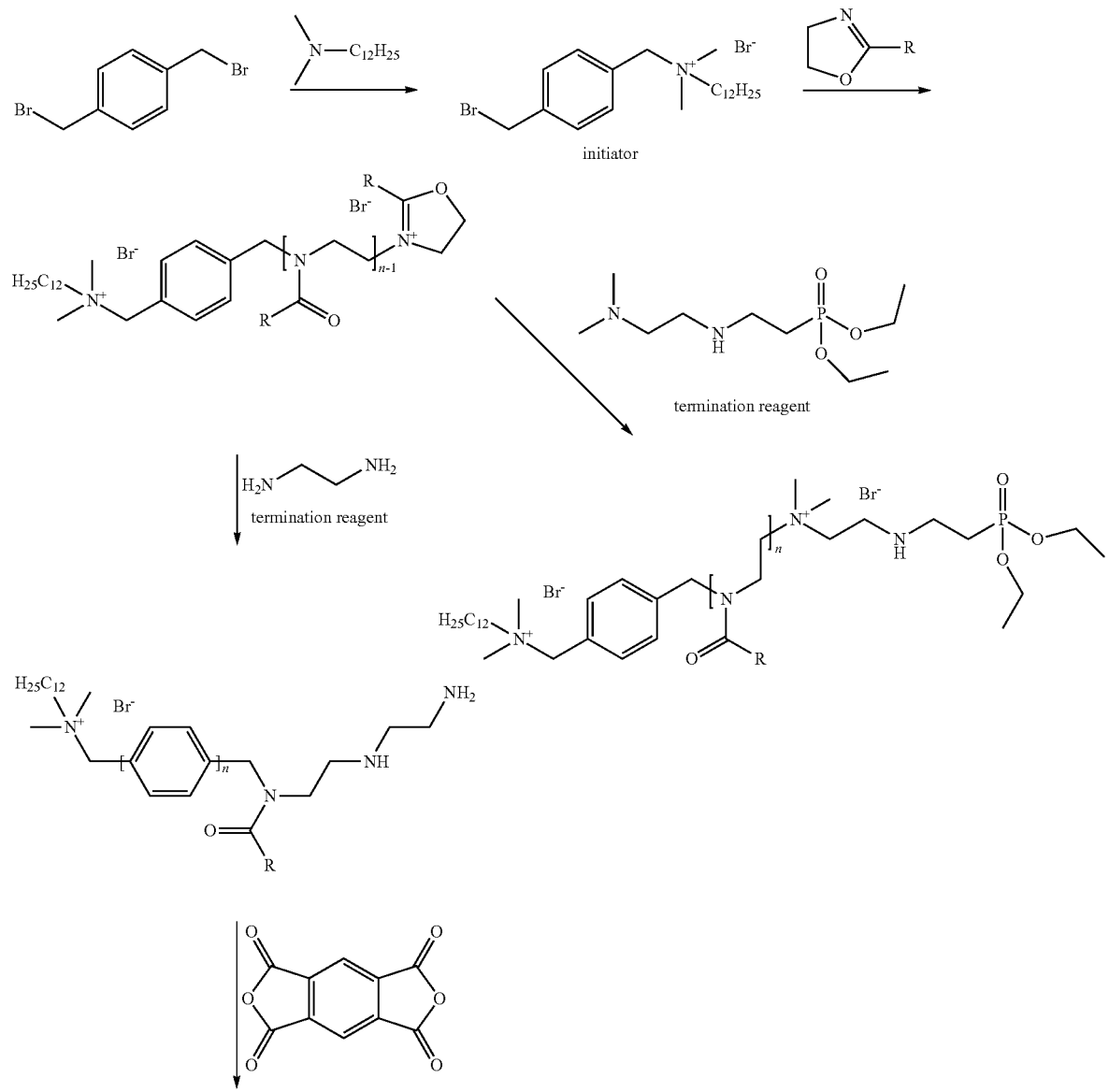

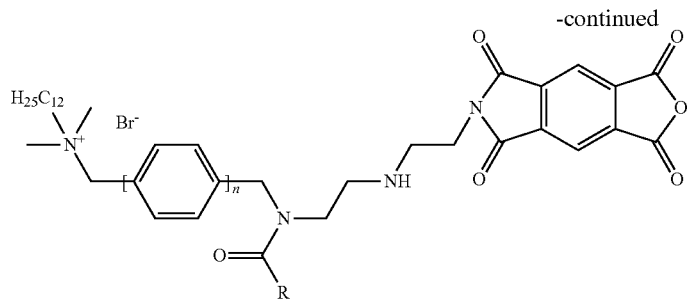

In a second synthesis variant, a compound which comprises an anchor group AG is used as initiator. Preferably, an amine that comprises an antimicrobially active group WG is used to terminate the polymerization. Particularly preferably, a tertiary amine is used to terminate the polymerization, whereby the corresponding quaternary ammonium group forms as antimicrobially active group WG.

A compound with a suitable protective group can also be used as initiator. In this case, depending on the selected synthesis variant, the antimicrobially active group WG or the anchor group AG is introduced after polymerization has finished and the protective group has been removed.

The compounds according to the invention of Formula (I) are suitable in particular for the preparation of a polymerizable dental restorative material. In a second aspect, the invention therefore relates to a dental restorative material which comprises
(a) at least one antimicrobially active compound of Formula (I) according to the first aspect of the invention, or a filler that is surface-modified with at least one compound of Formula (I) according to the first aspect of the invention;
(b) at least one radically polymerizable monomer; and
(c) at least one initiator for the radical polymerization.

Preferred embodiments of the compound of Formula (I) are as defined above for the first aspect of the invention.

Preferred radically polymerizable monomers are mono- or multifunctional (meth)acrylates or (meth)acrylamides ((meth)acrylic compounds). By monofunctional (meth) acrylic compounds are meant compounds with one, by polyfunctional (meth)acrylic compounds with two or more, preferably 2 to 3, (meth)acrylic groups. Polyfunctional monomers have cross-linking properties.

Preferred monofunctional (meth)acrylic compounds are commercially available monofunctional monomers, such as methyl, ethyl, butyl, benzyl, furfuryl or phenyl (meth)acrylate as well as 2-hydroxyethyl- or -propyl (meth)acrylate.

Particularly preferred are hydrolysis-stable monomers such as hydrolysis-stable mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as e.g. N-ethylacrylamide, N,N-dimethylacrylamide, N-(2-hydroxyethyl)acrylamide or N-methyl-N-(2-hydroxyethyl) acrylamide, and N-monosubstituted methacrylamides, such as e.g. N-ethylmethacrylamide or N-(2-hydroxyethyl)methacrylamide as well as N-vinylpyrrolidone and allyl ethers. These monomers are liquid at room temperature and are therefore also suitable as diluents.

Preferred polyfunctional monomers are bisphenol-A-di (meth)acrylate, bis-GMA (an addition product of methacrylic acid and bisphenol-A-diglycidyl ether), ethoxylated bisphenol-A-di(meth)acrylate, UDMA (an addition product of 2-hydroxyethyl methacrylate and 2,2,4-trimethyl hexamethylene diisocyanate), di-, tri- or tetraethylene glycol di(meth) acrylate, trimethylolpropane tri(meth)acrylate, pentaerythritol tetra(meth)acrylate, as well as butanediol di(meth) acrylate, 1,10-decanediol di(meth)acrylate, or 1,12-dodecanediol di(meth)acrylate.

Particularly preferred are furthermore hydrolysis-stable cross-linking monomers, such as e.g. cross-linking pyrrolidones, such as e.g. 1,6-bis-(3-vinyl-2-pyrrolidonyl)-hexane, or commercially available bisacrylamides such as methylene or ethylenebisacrylamide, bis-(meth)acrylamides, such as e.g. N,N'-diethyl-1,3-bis-(acrylamido)-propane, 1,3-bis-(methacrylamido)-propane, 1,4-bis-(acrylamido)-butane or 1,4-bis-(acryloyl)-piperazine, which can be synthesized by reaction of the corresponding diamines with (meth)acrylic acid chloride.

The dental restorative materials according to the invention preferably also comprise at least one radically polymerizable, acid-group-containing monomer. In the following, acid-group-containing monomers are also called acidic monomers. Preferred acid groups are carboxylic acid groups, phosphonic acid groups, phosphate groups and/or sulphonic acid groups, wherein these groups can be present in the acid form or in the form of an ester. Monomers with phosphonic acid groups or phosphate groups are particularly preferred. The monomers can have one or more acid groups, with compounds with 1 to 2 acid groups being preferred.

Preferred polymerizable carboxylic acids are maleic acid, acrylic acid, methacrylic acid, 2-(hydroxymethyl)acrylic acid, 4-(meth)acryloyloxyethyltrimellitic acid and the corresponding anhydride, 10-methacryloyloxydecylmalonic acid, N-(2-hydroxy-3-methacryloyloxypropyl)-N-phenylglycine and 4-vinylbenzoic acid.

Preferred phosphonic acid monomers are vinylphosphonic acid, 4-vinylphenylphosphonic acid, 4-vinylbenzylphosphonic acid, 2-methacryloyl-oxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid and 2-[2-dihydroxyphosphoryl)-ethoxymethyl]-acrylic acid-2,4,6-trimethyl-phenyl ester.

Preferred acidic polymerizable phosphoric acid esters are 2-methacryloyl-oxypropylmono- and -dihydrogen phosphate, 2-methacryloyl-oxyethylmono- and -dihydrogen phosphate, 2-methacryloyl-oxyethylphenyl-hydrogen phosphate, dipentaerythritol-pentamethacryloyloxyphosphate, 10-methacryloyloxydecyl-dihydrogen phosphate, dipentaerythritolpentamethacryloyloxyphosphate, phosphoric acid mono-(1-acryloyl-piperidine-4-yl)-ester, 6-(methacrylamido)hexyldihydrogen phosphate and 1,3-bis-(N-acryloyl-N-propyl-amino)-propan-2-yl-dihydrogen phosphate.

Preferred polymerizable sulphonic acids are vinyl sulphonic acid, 4-vinylphenyl sulphonic acid or 3-(methacrylamido)propyl sulphonic acid.

Acylphosphine oxides, bisacylphosphine oxides, benzophenone, benzoin as well as their derivatives or α-diketones or their derivatives such as 9,10-phenanthrenequinone, 1-phenyl-propan-1,2-dione, diacetyl or 4,4-dichlorobenzil are preferably used to initiate the radical photopolymerization. Camphorquinone and 2,2-methoxy-2-phenyl-acetophenone are preferably, and α-diketones combined with amines are particularly preferably, used as reducing agents, such as e.g. 4-(dimethylamino)-benzoic acid ester, N,N-dimethylaminoethylmethacrylate, N,N-dimethyl-sym.-xylidine or triethanolamine. Combinations of different photoinitiators are also used.

Redox-initiator combinations, such as e.g. combinations of benzoyl peroxide with N,N-dimethylsym.-xylidine or N,N-dimethyl-p-toluidine, are used as initiators for a so-called chemical curing. In addition, redox systems consisting of peroxides and reducing agents, such as e.g. ascorbic acid, barbiturates or sulphinic acids, are also particularly suitable.

Furthermore the dental restorative materials can comprise fillers to improve the mechanical properties or to set the viscosity. Particulate fillers are preferred as fillers according to the invention. Quite particularly preferred are organic or inorganic filler particles which have an average particle size [determined by transmission electron microscopy (about 10 to about 80 nm), scanning electron microscopy (about 50 nm to about 5 μm) or laser diffraction (about 0.1 to about 100 μm)] of abpit 10 nm to about 50 μm, particularly preferably about 10 nm to about 30 μm and quite particularly preferably about 10 nm to about 5 μm.

Preferred particulate fillers are amorphous spherical materials based on oxides, such as $ZrO_2$ and $TiO_2$, or mixed oxides of $SiO_2$, $ZrO_2$ and/or $TiO_2$ having an average particle size from about 10 nm to about 1 μm, nanoparticulate or microfine fillers such as pyrogenic silica or precipitated silica having an average particle size of about 10 nm to about 500 nm as well as minifillers, such as quartz, glass ceramic or glass powder having an average particle size of about 0.1 to about 5 μm, preferably about 0.2 to about 3 μm and quite particularly preferably about 0.4 to about 1.5 μm, as well as X-ray opaque fillers, such as ytterbium trifluoride or nanoparticulate tantalum (V) oxide or barium sulphate having an average particle size of about 10 nm to about 500 nm.

In one embodiment, the dental restorative material comprises at least one compound of Formula (I). Compounds of Formula (I) are preferred wherein the anchor group AG is selected from phosphonate, dialkylphosphonate, phosphate, sulphonic acid, carboxylic acid anhydride, carboxylic acid or aldehyde group. A dicarboxylic acid, carboxylic acid anhydride or phosphonate group is most preferred.

In another embodiment, the compound of Formula (I) is bonded to a filler. The dental restorative material thus preferably comprises at least one filler that is surface-modified with at least one antimicrobially active compound of Formula (I). Compounds of Formula (I) are preferred wherein AG is a silyl group —$SiR^{17a}R^{17b}R^{17c}$, wherein $R^{17a}$ is selected from alkoxy, aryloxy, Cl or OH, in particular alkoxy, aryloxy, preferably methoxy, ethoxy or propoxy and particularly preferably methoxy, and $R^{17b}$ and $R^{17c}$ are each independently selected from alkoxy, aryloxy, Cl, OH, alkyl or aryl, preferably alkoxy, aryloxy, alkyl or aryl, in particular alkoxy or aryloxy, preferably methoxy, ethoxy or propoxy and particularly preferably methoxy. Preferably at least one silicon atom from the AG group is covalently bonded to the filler via an oxygen atom bonded thereto.

In addition to the filler that is surface-modified with the compound of Formula (I), the dental restorative material can also comprise filler which is not modified with a compound of Formula (I). The filler is preferably selected from the fillers defined above. Likewise, the dental restorative material can also comprise, in addition to the compound of Formula (I) bonded to the filler, non-filler-bonded compound of Formula (I).

The filler portion that is not modified with a compound of Formula (I) is preferably surface-modified with polymerizable groups, for example with an alkoxysilane such as 3-(methacryloyloxy)propyltrimethoxysilane (MPTMS).

Moreover, the dental restorative materials according to the invention can comprise one or more further additives which are preferably selected from stabilizers, inhibitors, flavoring agents, dyes, pigments, fluoride-ion-releasing additives, optical brighteners, plasticizers and/or UV absorbers. A preferred UV absorber is 2-hydroxy-4-methoxybenzophenone, preferred stabilizers are 2,6-di-tert-butyl-4-cresol and 4-methoxyphenol.

The dental restorative materials according to the invention preferably comprise:
(a) about 0.05 to about 50 wt.-%, preferably about 0.5 to about 25 wt.-% and particularly preferably about 2 to about 10 wt.-% antimicrobially active compound of Formula (I);
(b) about 5 to about 95 wt.-%, preferably about 5 to about 85 wt.-% and particularly preferably about 5 to about 70 wt.-% radically polymerizable monomer; and
(c) about 0.01 to about 5 wt.-% and preferably about 0.1 to about 5 wt.-% initiator for the radical polymerization.

In addition to components (a) to (c), the dental restorative materials according to the invention preferably also comprise:
(d) 0 to about 60 wt.-%, preferably about 5 to about 50 wt.-% and particularly preferably about 5 to about 45 wt.-% acidic radically polymerizable monomer; and/or
(e) 0 to about 90 wt.-% and preferably about 1 to about 85 wt.-% filler; and/or
(f) 0 to about 99.95 wt.-%, preferably about 0.5 to about 60 wt.-% and particularly preferably about 1 to about 40 wt.-% solvent; and/or
(g) 0 to about 5 wt.-% and preferably about 0.01 to about 3.0 wt.-% further additives.

Dental restorative materials according to the invention wherein the antimicrobially active compound of Formula (I) is bonded to a filler preferably comprise:
(a) about 1 to about 60 wt.-% and preferably about 5 to about 40 wt.-% filler that is surface-modified with at least one antimicrobially active compound of Formula (I);
(b) about 5 to about 95 wt.-%, preferably about 5 to about 85 wt.-% and particularly preferably about 5 to about 70 wt.-% radically polymerizable monomer; and,
(c) about 0.01 -about 5.0 wt.-%, preferably about 0.1 to about 5.0 wt.-% initiator for the radical polymerization.

In addition to components (a) to (c), these dental restorative materials also preferably comprise:
(d) 0 to about 60 wt.-%, preferably about 5 to about 50 wt.-% and particularly preferably about 5 to about 45 wt.-% acidic radically polymerizable monomer; and/or
(e) 0 to about 40 wt.-% and preferably 0 to about 30 wt.-% filler that is not surface-modified with an antimicrobially active compound of Formula (I); and/or
(f) 0 to about 99.95 wt.-%, preferably about 0.5 to about 60 wt.-% and particularly preferably about 1 to about 40 wt.-% solvent; and/or
(g) 0 to about 5 wt.-% and preferably about 0.01 to about 3.0 wt.-% further additives.

The precise composition of the dental restorative materials according to the invention is based on the desired application. The dental restorative materials according to the invention are particularly suitable as filling materials and quite particularly as coating materials, adhesives, primers, self-adhesive and/or self-conditioning fixing cements.

Filling materials preferably have the following composition:
(a) about 0.05 to about 35 wt.-%, preferably about 0.5 to about wt.-% and particularly preferably about 2 to about 10 wt.-% compound of Formula (I);
(b) about 15 to about 25 wt.-% radically polymerizable monomer, preferably cross-linking monomer, in particular bis-GMA, urethane dimethacrylate and/or ethoxylated bis-GMA;
(c) about 0.5 to about 2.5 wt.-% initiator, preferably a camphorquinone/amine photoinitiator system, in particular about 0.2 to about 0.6 wt.-% camphorquinone and about 0.3 to about 0.6 wt.-% amine coinitiator;
(d) about 50 to about 80 wt.-% filler, preferably about 45 to about 65 wt.-% finely ground glass filler, in particular barium or strontium glass filler, and about 5 to about 25 wt.-% X-ray opaque filler, in particular ytterbium trifluoride;
(e) 0 to about 39 wt.-% of a ground prepolymer;
(f) 0 to about 0.5 wt.-%, preferably about 0.01-about 0.5 wt.-% coloring pigments.

Coating materials preferably have the following composition:
(a) about 0.05 to about 10 wt.-%, preferably about 0.1 to about 5 wt.-% and particularly preferably about 0.5 to about 2.5 wt.-% compound of Formula (I);
(b) about 50 to about 90 wt.-%, preferably about 65 to about 85 wt.-% radically polymerizable monomer, preferably about 60.0-about 70.0 wt.-% cross-linking monomer, in particular triacrylate, and about 8.0 to about 15.0 wt.-% diluting monomer, in particular methyl methacrylate;
(c) about 0.5 to about 2.5 wt.-% initiator, preferably a camphorquinone/amine photoinitiator system, in particular about 0.2 to about 0.6 wt.-% camphorquinone and about 0.3 to about 0.6 wt.-% amine coinitiator and about 0.5 to about 1.2 wt.-% 2,4,6-trimethylbenzoyldiphenylphosphine oxide;
(d) about 5.0 to about 15 wt.-% filler, in particular $SiO_2$ nanoparticles;
(e) 0 to about 10.0 wt.-% organic solvent.

Adhesives and primers preferably have the following composition:
(a) about 0.05 to about 10 wt.-%, preferably about 0.1 to about wt.-% and particularly preferably about 0.5-about 1.5 wt.-% compound of Formula (I);
(b) about 10 to about 20 wt.-% cross-linking monomer, in particular glycerol dimethacrylate (GDMA) or triethylene glycol dimethacrylate (TEGDMA);
(c) about 30 to about 50 wt.-% hydrophilic monomer, preferably 2-hydroxyethyl methacrylate (HEMA);
(d) about 20 to about 30 wt.-% acidic monomer, preferably methacryloyloxydecyl dihydrogen phosphate (MDP);
(e) about 0.5 to about 2.5 wt.-% initiator, preferably a camphorquinone/amine photoinitiator system, in particular 0.2 to 0.6 wt.-% camphorquinone and 0.3 to 0.6 wt.-% amine coinitiator, in particular ethyl-p-dimethylaminobenzoate;
(f) about 5 to about 20 wt.-% of an organic solvent, preferably ethanol.

Self-adhesive and/or self-conditioning fixing cements preferably have the following composition:
Base Paste:
(a) about 0.05 to about 20 wt.-%, preferably about 0.1 to about 10 wt.-% and particularly preferably about 0.5-about 5 wt.-% compound of Formula (I);
(b) about 25 to about 40 wt.-% radically polymerizable monomer, preferably cross-linking monomer, in particular triethylene glycol dimethacrylate (TEGDMA) or urethane dimethacrylate (UDMA);
(c) about 1 to about 3.5 wt.-% amine, preferably N,N-di(2-hydroxy)-p-toluidine; and
(d) about 15 to about 70 wt.-% filler, preferably about 2 to about 5.5 wt.-% $SiO_2$ particles, about 5 to about 25 wt.-% X-ray opaque filler, in particular ytterbium trifluoride, about 10 to about 45 wt.-% splinter polymerisate and 0 to about 45 wt.-% finely ground glass filler, in particular barium or strontium glass filler.

Catalyst Paste:
(a) about 3 to about 8 wt.-% acidic monomer, preferably methacryloyloxydecyl dihydrogen phosphate (MDP);
(b) about 25 to about 37 wt.-% radically polymerizable monomer, preferably cross-linking monomer, in particular triethylene glycol dimethacrylate (TEGDMA) or urethane dimethacrylate (UDMA);
(c) about 0.5 to about 3 wt.-% peroxide, preferably dibenzoyl peroxide;
(d) about 0.5 to about 2.5 wt.-% camphorquinone/amine photoinitiator system; and
(e) about 20 to about 70 wt.-% filler, preferably about 5 to about 25 wt.-% X-ray opaque filler, in particular ytterbium trifluoride, about 2 to about 5.5 wt.-% $SiO_2$ particles, about 10 to about 45 wt.-% splinter polymerisate and about 5 to about 45 wt.-% finely-ground glass filler, in particular barium glass or strontium glass filler.

Compounds according to the invention of Formula (I) are also suitable for the direct treatment of hard tooth structure such as tooth enamel and dentine, collagen, soft tissue, mucous membrane etc. Depending on the application, the compounds of Formula (I) can be used for cosmetic or medical purposes.

In a third aspect, the invention therefore relates to a dental material which comprises at least one compound of Formula (I) according to the first aspect of the invention. Furthermore, the invention also relates to the use of a compound of Formula (I) according to the first aspect of the invention as a dental material or for the preparation of a dental material, in particular for the antimicrobial treatment of teeth and/or dental restorations. Compounds of Formula (I) are particularly preferred wherein AG is selected from phosphonate, phosphate, carboxylic acid, trimellitic acid, pyromellitic acid monoimide, carboxylic acid anhydride, trimellitic acid anhydride, pyromellitic acid monoimide anhydride, succinic anhydride, sulphonic acid, sulphonate, isocyanate, formiate, formamide, β-ketoester, aldehyde, hemiacetal, acetal, imidoester, N-hydroxysuccinimide ester, sulfosuccinimide ester, maleimide and carbodiimide groups, preferably phosphonate, in particular dialkylphosphonate, phosphate, carboxylic acid, carboxylic acid anhydride and sulphonic acid groups, most preferably multifunctional carboxylic acid groups, in particular di, tri and tetracarboxylic acid groups, carboxylic acid anhydride groups and phosphonate groups. Further preferred embodiments of the compound of Formula (I) are as defined above for the first aspect of the invention.

The dental material preferably has the form of a mouthwash solution, a toothpaste, a tooth gel, a tooth tincture or a tooth varnish. Particularly preferred dental materials have the following compositions:

Tooth Gel:
(a) about 0.05 to 10 wt.-%, preferably about 0.1 to about 5 wt.-% and particularly preferably about 0.5 to about 2.5 wt.-% compound of Formula (I);

(b) 0 to about 2 wt.-% and preferably about 0.05 to about 1.5 wt.-% flavouring agent, in particular peppermint oil and/or methyl salicylate (wintergreen oil);
(c) 0 to about 2.5 wt.-%, preferably about 0.5 to about 2 wt.-% gelling agent, in particular hydroxymethyl cellulose and/or xanthan; and
(d) about 90 to about 95 wt.-% and preferably 91 to 95 wt.-% water.

Tooth Tincture:
(a) about 0.05 to about 20 wt.-%, preferably about 0.1 to about 15 wt.-% and particularly preferably about 0.5 to about 10 wt.-% compound of Formula (I);
(b) 0 to about 2 wt.-% and preferably about 0.05 to about 1.5 wt.-% flavouring agent, in particular peppermint oil and/or methyl salicylate (wintergreen oil);
(c) 0 to about 2.5 wt.-%, preferably about 0.5 to about 2 wt.-% gelling agent, in particular hydroxymethyl cellulose and/or xanthan;
(d) about 5 to about 55 wt.-% and preferably about 6 to about 55 wt.-% water;
(e) about 25 to about 75 wt.-% organic solvent, preferably ethanol, isopropanol or acetone.

Furthermore, the compounds of Formula (I) are suitable for providing surfaces with antimicrobial properties, in particular substrates for example of ceramic materials, such as siliceous ceramics, aluminium oxide, zirconium oxide and noble and non-noble metals. In addition, the compounds of Formula (I) are also suitable for the treatment of further substrates, for example natural products such as leather, in order to give them antiseptic properties. The compounds are usually used dissolved in a solvent.

In a fourth aspect, the invention therefore relates to the use of a compound of Formula (I) according to the first aspect of the invention for modifying the surface of a substrate. The substrate is preferably selected from ceramic materials, such as siliceous ceramics, aluminium oxide, zirconium oxide and noble and non-noble metals. It is further preferred that the substrate has the form of a dental restoration, such as e.g. a crown, a bridge, an inlay, an onlay, an implant abutment, a full or partial prosthesis. Preferred embodiments of the compound of Formula (I) are as defined above for the first aspect of the invention.

The invention is explained in more detail below by means of examples.

EXAMPLES

Example 1

Preparation of a Compound of Formula (I) with Polyalkyloxazoline Spacer and Pyromellitic Acid Monoimide Anhydride Anchor Group

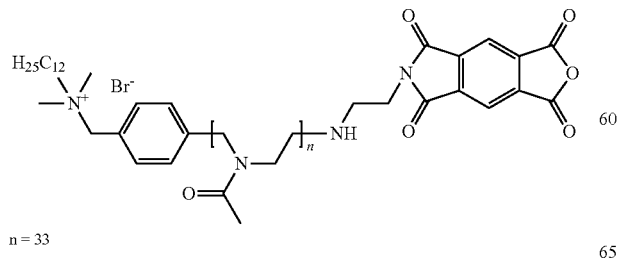

n = 33

1.1. Preparation of Starter Compound 1 with Quaternary Alkylammonium Group

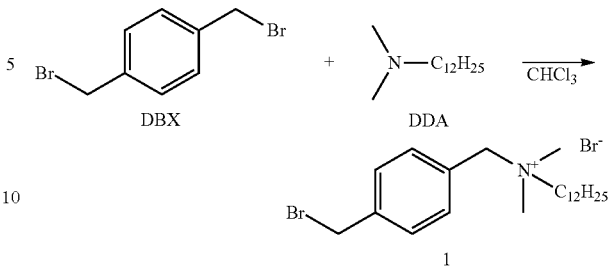

The commercial educts α,α'-dibromo-p-xylene (DBX) and N,N-dimethyldodecylamine (DDA) were purified before use by double recrystallization from CHCl$_3$. In a reaction flask, DBX (5.00 g, 18.94 mmol, 1.0 eq.) was dissolved in small portions in dry CHCl$_3$ (100 ml) at 25° C. with vigorous stirring. The solution was then stirred such that laminar flow only just prevailed in the flask, and the temperature was adjusted to 25° C. by means of a water bath. In a dropping funnel (25 ml) DDA (2.565 ml, 9.47 mmol, 0.5 eq.) was diluted with dry CHCl$_3$ to 10.0 ml in total. The diluted DDA was added dropwise very slowly over 45 min to the solution of DBX, and the mixture was stirred for a further 15 min. The reaction mixture was concentrated to approx. 30% v/v on the rotary evaporator and any precipitating solid (educt, minimum quantity) was separated off by means of filtration. The remaining clear supernatant was added to THF (200 ml) with stirring, and the resulting dispersion was separated by means of centrifugation (10 min, 5,000 rpm). The sedimented white solid (by-product) was discarded. The homogeneous THF phase was concentrated to approx. 50% v/v and the above procedure was carried out five times in total. After removal of the remaining solvent, the pure product 1 was obtained as a yellowish-brown, highly viscous substance.

1.2. Polymerization of Methyloxazoline by Initiation with Starter Compound 1 and Termination with Ethylenediamine 2

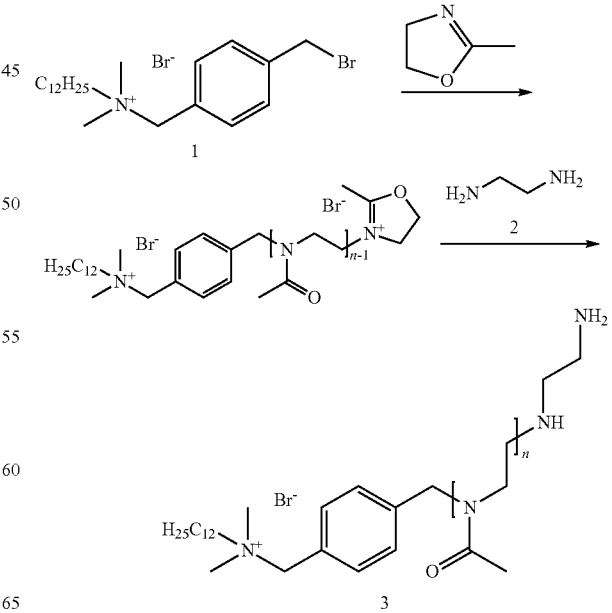

The starter compound (1, 0.56 g, 1.17 mmol, 1.0 eq.) was dissolved in dry CHCl₃ (18 ml, 20° C., [Ar]) and transferred to a pressure-resistant glass reactor (50 ml). Methyloxazoline (3.00 g, 3.00 ml, 35.2 mmol, 30.0 eq.) was added. The polymerization (4 h) was carried out with dielectric heating (100° C.) in a polymerization microwave (300 W). Ethylenediamine (2, 1.41 g, 1.57 ml, 23.4 mmol, 20.0 eq.) was added and the reaction mixture was stirred in a water bath (24 h, 40° C.). The amine-functionalized polymer was obtained by reprecipitating five times from CHCl₃ in diethyl ether as a yellowish, hygroscopic powder (3, $DP_{NMR}$=33, 3.35 g, 93%). The characterization was performed by means of ¹H- and ¹³C-NMR as well as GPC.

1.3. Polymer-Analogous Reaction of Poly(Methyloxazoline) 3 with the Pyromellitic Anchor Group in DMF

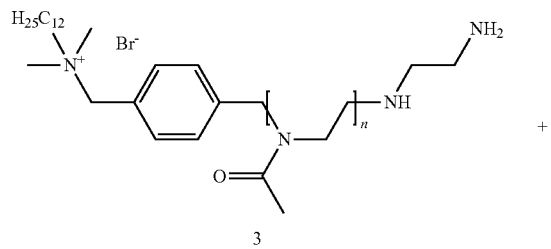

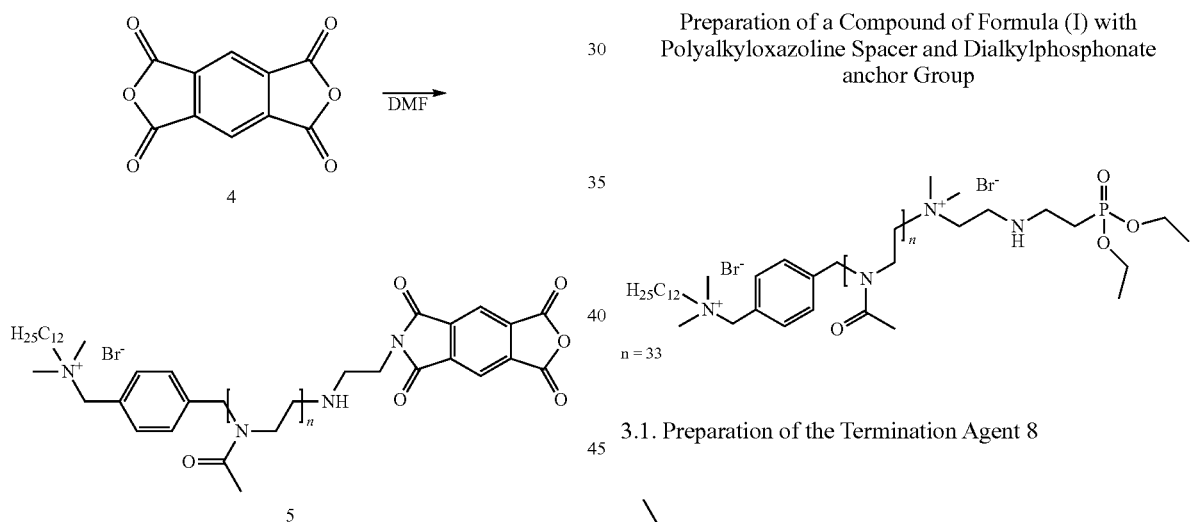

Pyromellitic acid dianhydride (4, 3.96 g, 18.2 mmol, 20.0 eq.) was dissolved in DMF (60 ml, 30° C.) and cooled to 0° C. by means of an ice bath. The amine-terminated poly(methyloxazoline) 3 (3.00 g, 0.91 mmol, 1.0 eq.) was dissolved in dry DMF (40 ml, 0° C., residual moisture <3 ppm after distillation/drying over basic aluminium oxide). The polymer solution was quickly added dropwise to the compound 4. The mixture was stirred for 5 min. The reacted polymer was obtained by reprecipitating five times from DMF in diethyl ether as a yellow-brownish, hygroscopic powder (5, $DP_{NMR}$=33, 2.95 g, 92%). The characterization was performed by means of ¹H- and ¹³C-NMR as well as GPC.

Example 2

Preparation of a Compound of Formula (I) with Polyalkyloxazoline Spacer and Pyromellitic Acid Monoimide Anchor Group

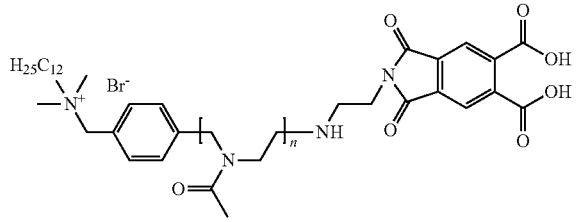

n = 33

By hydrolysis of the anhydride 5 from Example 1, the corresponding dicarboxylic acid was obtained.

The hydrolysis was effected by stirring in distilled water at room temperature. The product was obtained by concentrating the solution and spray-drying or precipitation at low temperature.

Example 3

Preparation of a Compound of Formula (I) with Polyalkyloxazoline Spacer and Dialkylphosphonate anchor Group 3.1. Preparation of the Termination Agent 8

Diethyl-2-bromoethylphosphonate (6, 10.0 g, 40.8 mmol, 1.0 eq.) was dissolved in dry CHCl₃ (10 ml, 20° C.). N,N- dimethylethane-1,2-diamine (7, 3.60 g, 40.8 mmol, 1.0 eq.) in CHCl$_3$ (10 ml, 20° C.) was then slowly added dropwise over 15 min with stirring.

The reaction mixture was precipitated in diethyl ether and the thus obtained raw product was purified by reprecipitating three times from methanol in diethyl ether. The pure product was obtained as a yellow-white, pasty substance (8, 9.1 g, 88%). The characterization was performed by means of $^1$H- and $^{13}$C-NMR.

3.2. Polymerization of Methyloxazoline, Initiation by Starter Compound 1, Termination with Aminophosphonate 8

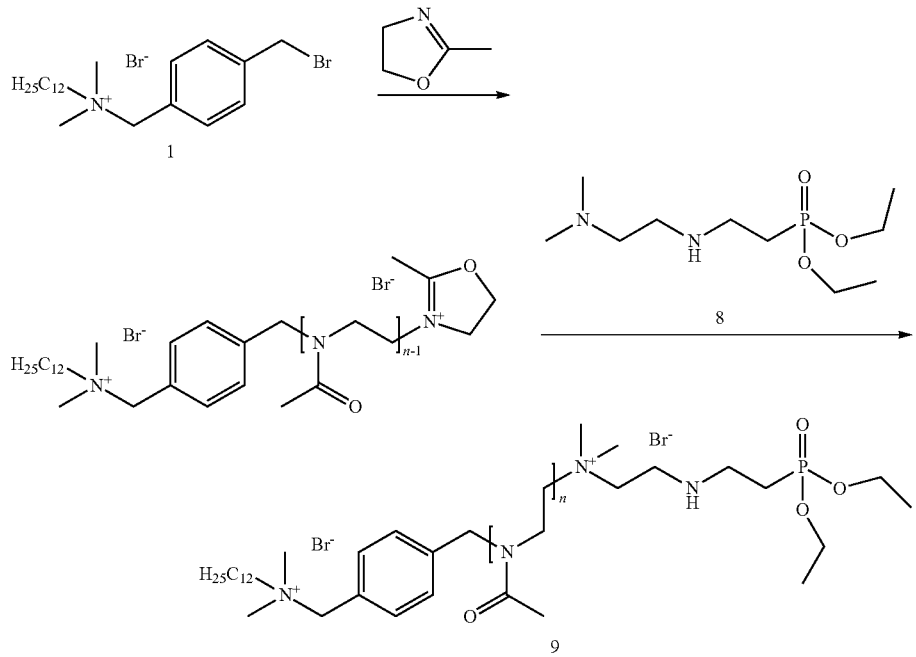

The starter compound from Example 1 (1, 0.56 g, 1.17 mmol, 1.0 eq.) was dissolved in dry CHCl$_3$ (18 ml, 20° C., [Ar]) and transferred into a pressure-resistant glass reactor (50 ml). Methyloxazoline (3.00 g, 3.00 ml, 35.2 mmol, 30.0 eq.) was added. The polymerization (4 h) was carried out with dielectric heating (100° C.) in a polymerization microwave (300 W).

Termination agent (8, 5.90 g, 23.4 mmol, 20.0 eq.) was added and the reaction mixture was diluted with further CHCl$_3$ (10 ml) and stirred in a water bath (48 h, 40° C.)

The aminophosphonate-functionalized polymer was obtained by reprecipitating five times from CHCl$_3$ in diethyl ether as a yellowish, hygroscopic powder (9, DP$_{NMR}$=33, 3.95 g, 95%). The characterization was performed by means of $^1$H- and $^{13}$C-NMR as well as GPC.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:
1. Dental restorative material which comprises
(a) at least one antimicrobially active compound of Formula (I)

$$[AG]_m - R^1 - Z - SP - Y - R^2 - [WG]_p \qquad (I),$$

wherein the variables have the following meanings:

m=1, 2, 3 or 4;

p=1, 2 or 3;

$R^1$=is absent or a linear or branched C$_1$ to C$_{20}$ alkylene radical which can be interrupted one or more times by O, S, NH, N$^+$R$^3_2$, SiR$^3_2$, OSiR$^3_2$, CONH, CONR$^3$, COO and/or OCONH, a substituted or unsubstituted, aromatic C$_6$ to C$_{14}$ radical or a combination thereof;

$R^2$=is absent or a linear or branched C$_1$ to C$_{20}$ alkylene radical which can be interrupted one or more times by O, S, NH, N$^+$R$^3_2$, SiR$^3_2$, OSiR$^3_2$, CONH, CONR$^3$, COO and/or OCONH, a substituted or unsubstituted, aromatic C$_6$ to C$_{14}$ radical or a combination thereof;

$R^3$=in each case independently a linear or branched C$_1$ to C$_{20}$ alkyl radical, a substituted or unsubstituted phenyl or benzyl radical;

AG=an anchor group selected from:

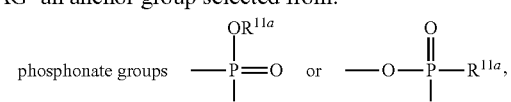

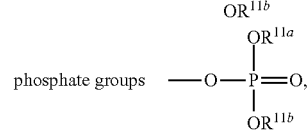

wherein R$^{11a}$ and R$^{11b}$ are independently selected from H, alkyl, aryl or —Si(alkyl)$_3$,

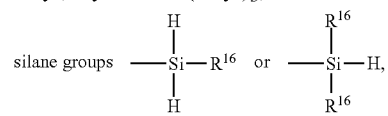

wherein R$^{16}$ is independently selected from alkoxy, aryloxy, Cl, alkyl or aryl, silyl groups 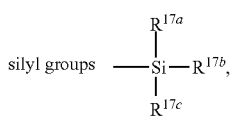

wherein $R^{17a}$ is selected from alkoxy, aryloxy, Cl or OH, and $R^{17b}$ and $R^{17c}$ are each independently selected from alkoxy, aryloxy, Cl, OH, alkyl or aryl, WG=an antimicrobially active group;

Y=is absent, O, S, NH, $N^+R^3{}_2$, an ester, amide or urethane group,

Z=is absent, O, S, NH, $N^+R^3{}_2$, an ester, amide or urethane group;

or a filler that is surface-modified with at least one compound of Formula (I);

(b) at least one radically polymerizable monomer; and (c) at least one initiator for the radical polymerization.

2. Dental restorative material according to claim 1, wherein $R^1$ and/or $R^2$ is a linear or branched $C_5$ to $C_{20}$ alkylene radical.

3. Dental restorative material according to claim 1, wherein AG is selected from phosphonate and phosphate groups.

4. Dental restorative material according to claim 1, wherein the antimicrobially active group WG comprises a pyridinium group of formula

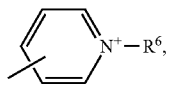

which is attached in ortho, meta or para position to the rest of the compound of Formula (I), or a pyridinium group of formula

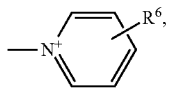

which can be substituted with $R^6$ in ortho, meta or para position, wherein $R^6$ in each case independently represents H or a linear or branched $C_1$ to $C_{20}$ alkyl radical;

$N^+R^7R^8R^9$ $A^-$, with $R^7$=H, a linear or branched $C_1$ to $C_{20}$ alkyl radical;

$R^8$=H, a linear or branched $C_1$ to $C_{20}$ alkyl radical;

or $R^7$ and $R^8$ together with the nitrogen atom to which they are bonded form an aromatic or non-aromatic ring system or an aromatic or non-aromatic ring;

$R^9$=is absent, H, a linear or branched $C_1$ to $C_{31}$ alkyl radical;

r=5 to 30;

$A^-$=$F^-$, $Cl^-$, $Br^-$, $I^-$, triflate (Trf), mesylate (Mes), tosylate (Tos), palmitate, stearate, gluconate, hexafluorophosphate, phenolate, (meth) acrylphosphonate, phosphate, hydrogen phosphate or dihydrogen phosphate;

—$P^+R^{7'}R^{9'}R^{9'}$ $A^-$, with $R^{7'}$=H, a linear or branched $C_1$ to $C_{20}$ alkyl radical;

$R^{8'}$=H, a linear or branched $C_1$ to $C_{20}$ alkyl radical;

$R^{9'}$=is absent, H, a linear or branched $C_1$ to $C_{31}$ alkyl radical;

r=5 to 30;

$A^-$=$F^-$, $Cl^-$, $Br^-$, $I^-$, triflate (Trf), mesylate (Mes), tosylate (Tos), palmitate, stearate, gluconate, hexafluorophosphate, phenolate, (meth)acrylphosphonate, phosphate, hydrogen phosphate or dihydrogen phosphate;

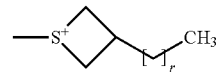

$A^-$ with r=5 to 30; or $A^-$=$F^-$, $Cl^-$, $Br^-$, $I^-$, triflate (Trf), mesylate (Mes), tosylate (Tos), palmitate, stearate, gluconate, hexafluorophosphate, phenolate, (meth)acrylphosphonate, phosphate, hydrogen phosphate or dihydrogen phosphate;

a quaternary alkylphosphonium or alkylsulphonium group, octenidine or a derivative thereof, chlorhexidine or another bisguanidine, triclosan or another chlorophenol, an inorganic group with antimicrobial properties.

5. Dental restorative material according to claim 1, wherein the antimicrobially active group WG is a quaternary alkylammonium group of formula

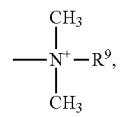

wherein $R^9$ is $C_1$ to $C_{31}$ alkyl.

6. Dental restorative material according to claim 1, wherein the spacer SP is a polyoxazoline, polyester, polyamide, polyurea, polyurethane, polycyanoacrylate, polyacrylate, polyacrylic ester, polymethacrylate, polymethacrylic ester, N-alkylated polyethyleneimine, N-alkylated vinylpyridine or polyaminosaccharide.

7. Dental restorative material according to claim 1, wherein the spacer SP is a polyoxazoline group of formula:

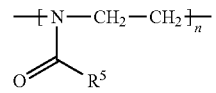

wherein n is 3 to 500 and $R^5$ is —$CH_3$, —$C_2H_5$ or —$C_3H_7$.

8. Dental restorative material according to claim 1, wherein at least one of the variables has one of the following meanings:

m=1 or 2;

p=1 or 2;

$R^1$=a linear or branched $C_1$ to $C_{20}$ alkylene radical which can be interrupted one or more times by O, S, NH, $N+R^3{}_2$, $SiR^3{}_2$, CONH, $CONR^3$, COO and/or OCONH;

$R^2$=a substituted or unsubstituted, aromatic $C_6$ to $C_{14}$ radical;

$R^3$=a linear or branched $C_1$ to $C_{20}$ alkyl radical;

SP=a polyoxazoline, polyester, polyamide, polyurea, polyurethane, polycyanoacrylate, polyacrylate, polyacrylic ester, polymethacrylate or polymethacrylic ester group;

AG=a phosphonate or phosphate group;

WG=a pyridinium group of formula

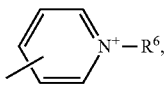

which is attached in ortho, meta or para position to the rest of the compound of Formula (I) or
a pyridinium group of formula

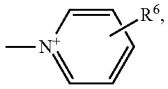

which can be substituted with $R^6$ in ortho, meta or para position,
wherein $R^6$ in each case independently represents H or a linear or branched $C_1$ to $C_{20}$ alkyl radical;
—$N^+R^7R^8R^9$ $A^-$, with
$R^7$=H, a linear or branched $C_1$ to $C_{20}$ alkyl radical;
$R^8$=H, a linear or branched $C_1$ to $C_{20}$ alkyl radical;
or $R^7$ and $R^8$ together with the nitrogen atom to which they are bonded form a heteroaromatic ring system or an aromatic or non-aromatic ring,
$R^9$=is absent, H, a linear or branched $C_1$ to $C_{31}$ alkyl radical;
r=5 to 30;
$A^-$=$F^-$, $Cl^-$, $Br^-$, $I^-$, triflate (Trf), mesylate (Mes), tosylate (Tos), palmitate, stearate, gluconate, hexa-fluorophosphate, phenolate, (meth) acrylphosphonate, phosphate, hydrogen phosphate or dihydrogen phosphate;
—$P^+R^{7'}R^{8'}R^{9'}$ $A^-$, with
$R^{7'}$=H, a linear or branched $C_1$ to $C_{20}$ alkyl radical;
$R^{8'}$=H, a linear or branched $C_1$ to $C_{20}$ alkyl radical;
$R^{9'}$=is absent, H, a linear or branched $C_1$ to $C_{31}$ alkyl radical;
r=5 to 30;
$A^-$=$F^-$, $Cl^-$, $Br^-$, $I^-$, triflate (Trf), mesylate (Mes), tosylate (Tos), palmitate, stearate, gluconate, hexa-fluorophosphate, phenolate, (meth) acrylphosphonate, phosphate, hydrogen phosphate or dihydrogen phosphate;

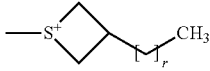

$A^-$ with
r=5 to 30; or
$A^-$=$F^-$, $Cl^-$, $Br^-$, $I^-$, triflate (Trf), mesylate (Mes), tosylate (Tos), palmitate, stearate, gluconate, hexa-fluorophosphate, phenolate, (meth) acrylphosphonate, phosphate, hydrogen phosphate or dihydrogen phosphate;
a quaternary alkylphosphonium or alkylsulphonium group, octenidine, chlorhexidine or another bisguanidine, triclosan or another chlorophenol, an inorganic group with antimicrobial properties, or an antimicrobial peptide group;
Y=is absent, O, S, COO;
Z is absent, O, S, NH, $N^+R^3_2$ or amide;
wherein all variables can be selected independently of one another.

9. Dental restorative material according to claim 1, which comprises a filler that is surface-modified with at least one compound of Formula (I).

10. Dental restorative material according to claim 9, wherein the filler is a particulate organic or inorganic filler, having an average particle size of about 10 nm to about 50 μm.

11. Dental restorative material according to claim 10, wherein the particulate organic or inorganic filler has a particle size of about 10 nm to about 30 μm.

12. Dental restorative material according to claim 11, wherein the particulate organic or inorganic filler has a particle size of about 10 nm to about 5 μm.

13. Dental restorative material according to claim 1, which comprises
(a) about 0.05 to about 50 wt.-% antimicrobially active compound of Formula (I);
(b) about 5 to about 95 wt.-% radically polymerizable monomer; and
(c) about 0.01 to about 5 wt.-% initiator for the radical polymerization.

14. Dental restorative material according to claim 1, which comprises
(a) about 0.5 to about 25 wt.-% antimicrobially active compound of Formula (I);
(b) about 5 to about 85 wt.-% radically polymerizable monomer; and
(c) about 0.1 to about 5 wt.-% initiator for the radical polymerization.

15. Dental restorative material according to claim 1, which comprises
(a) about 2 to about 10 wt.-% antimicrobially active compound of Formula (I);
(b) about 5 to about 70 wt.-% radically polymerizable monomer; and
(c) about 0.01 to about 5 wt.-% initiator for the radical polymerization.

16. Dental restorative material according to claim 13, which further comprises
(d) 0 to about 60 wt.-% acidic radically polymerizable monomer, and/or
(e) 0 to about 90 wt.-% filler, and/or
(f) 0 to about 99.95 wt.-% solvent, and/or
(g) 0 to about 5 wt.-% further additives.

17. Dental restorative material according to claim 13, which further comprises
(d) about 5 to about 50 wt.-% acidic radically polymerizble monomer, and/or
(e) about 1 to about 85 wt.-% filler, and/or
(f) about 0.5 to about 60 wt.-% solvent, and/or
(g) about 0.01 to about 3.0 wt.-% further additives.

18. Dental restorative material according to claim 13, which further comprises
(d) about 5 to about 45 wt.-% acidic radically polymerizale monomer, and/or
(e) about 1 to about 85 wt.-% filler, and/or
(f) about 1 to about 40 wt.-% solvent, and/or
(g) about 0.01 to about 3.0 wt.-% further additives.

19. Dental material which comprises at least one compound of Formula (I) as defined in claim 1.

20. Dental restorative material according to claim 1, wherein AG is an anchor group selected from:

thiophosphonate groups 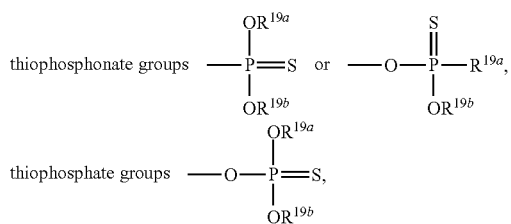

thiophosphate groups 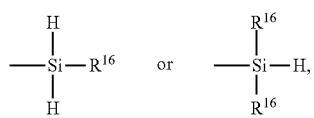

wherein $R^{11a}$ and $R^{11b}$ are each alkyl or $R^{11a}$ is H and $R^{11b}$ is alkyl, silane groups

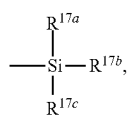

wherein $R^{16}$ is independently selected from alkoxy and aryloxy, silyl groups

wherein $R^{17a}$ is selected from alkoxy and aryloxy and $R^{17b}$ and $R^{17c}$ are each independently selected from alkoxy, aryloxy, alkyl and aryl.

21. Dental restorative material according to claim 1, wherein the spacer SP is a polymeric spacer group selected from polymers and copolymers of ethylene glycol groups, propylene glycol groups, glycerol groups, alkyloxazoline groups, ethyleneimine groups, acrylic acid groups, methacrylic acid groups, vinyl alcohol groups, vinyl acetate groups, (2 hydroxyethyl)acrylate groups, (2-hydroxy-ethyl)-methacrylate groups, hydrophilic peptide groups, oxazoline groups, alkylene groups, ester groups, amide groups, urea groups, urethane groups, cyanoacrylate groups, acrylate groups, acrylic ester groups, methacrylate groups, methacrylic ester groups, N-alkylated ethyleneimine groups, N-alkylated vinylpyridine groups, saccharide groups, aminosaccharide groups.

22. Dental restorative material according to claim 2, wherein $R^1$ and/or $R^2$ is a linear or branched $C_{10}$ to $C_{20}$ alkylene radical.

23. Dental restorative material according to claim 8, wherein at least one of the variables has one of the following meanings:
   m=1;
   p=1;
   $R^1$ =—$CH_2$—$CH_2$— or —$CH_2$—$CH_2$—NH—$CH_2$—$CH_2$—;
   $R^2$=phenylene or —$CH_2$-Ph-$CH_2$—;
   $R^3$=methyl, ethyl, n-propyl or i-propyl;
   SP=a polyoxazoline, polyester, polyamide, polyurea, polyurethane, polycyanoacrylate, polyacrylate, polyacrylic ester, polymethacrylate or polymethacrylic ester group;
   AG=a phosphonate or phosphate group;
   WG=a pyridinium group of formula

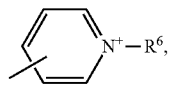

which is attached in para position to the rest of the compound of Formula (I) or
a pyridinium group of formula

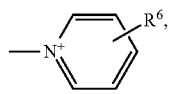

which can be substituted with $R^6$ in para position,
wherein $R^6$ in each case independently represents H or a linear or branched $C_1$ to $C_{20}$ alkyl radical;
—$N^+R^7R^8R^9$ $A^-$, with
$R^7$=—$CH_3$;
$R^8$=—$CH_3$;
or $R^7$ and $R^8$ together with the nitrogen atom to which they are bonded form a ring selected from

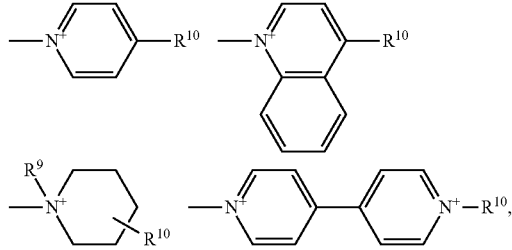

wherein $R^{10}$ is a linear or branched $C_1$ to $C_{20}$ alkyl radical;
$R^9$=—$(CH_2)_r$—$CH_3$;
r=10 to 20;
$A^-$=$F^-$, $Cl^-$, $Br^-$, $I^-$, triflate (Trf), mesylate (Mes) or tosylate (Tos);
—$P^+R^{7'}R^{8'}R^{9'}$ $A^-$, with
$R^{7'}$=—$CH_3$;
$R^{8'}$=—$CH_3$;
$R^{9'}$=—$(CH_2)_r$—$CH_3$;
r=10 to 20;
$A^-$=$F^-$, $Cl^-$, $Br^-$, $I^-$, triflate (Trf), mesylate (Mes) or tosylate (Tos);

—S⁺⟨⟩—$(CH_2)_r$—$CH_3$ $A^-$ with
r=10 to 20; or
$A^-$=$F^-$, $Cl^-$, $Br^-$, $I^-$, triflate (Trf), mesylate (Mes) or tosylate (Tos);
a quaternary alkylphosphonium or alkylsulphonium group, octenidine, chlorhexidine or another bisguanidine, triclosan or another chlorophenol, an inorganic group which comprises one or more antimicrobially active metal ions or an antimicrobial peptide group;
Y is absent;
Z is absent, NH, or $N^+(CH_3)_2$;

wherein all variables can be selected independently of one another.

24. Dental restorative material according to claim 9, wherein AG is a silyl group —SiR$^{17a}$R$^{17b}$R$^{17c}$, wherein R$^{17a}$ is selected from alkoxy, aryloxy, Cl or OH and R$^{17b}$ and R$^{17c}$ are each independently selected from alkoxy, aryloxy, Cl, OH, alkyl or aryl.

* * * * *